United States Patent [19]

Mich et al.

[11] Patent Number: 4,604,401
[45] Date of Patent: Aug. 5, 1986

[54] ANTIBACTERIAL AGENTS III

[75] Inventors: Thomas F. Mich; Townley P. Culbertson, both of Ann Arbor; John M. Domagala, Canton, all of Mich.

[73] Assignee: Warner-Lambert Company, Morris Plains, N.J.

[21] Appl. No.: 633,151

[22] Filed: Jul. 20, 1984

[51] Int. Cl.$^4$ .................. A61K 31/47; C07D 215/22
[52] U.S. Cl. .................................... 514/312; 546/15; 546/16; 546/156; 548/409; 548/410
[58] Field of Search .................. 424/258; 546/156, 15, 546/16; 514/312

[56] References Cited

U.S. PATENT DOCUMENTS 4,398,029  8/1983  Irikura .................................. 546/156

FOREIGN PATENT DOCUMENTS 90424   10/1983  European Pat. Off. .
1086476  1/1975  Japan .
5040656  9/1978  Japan .

Primary Examiner—Donald G. Daus
Assistant Examiner—Robert Benson
Attorney, Agent, or Firm—Elizabeth M. Anderson

[57] ABSTRACT

Novel 1-amino-naphthyridine- and quinoline-carboxylic acids as antibacterial agents are described as well as methods for their manufacture, formulation, and use in treating bacterial infections.

7 Claims, No Drawings

ANTIBACTERIAL AGENTS III

BACKGROUND OF THE INVENTION

U.S. Pat. No. 4,341,784 discloses certain substituted 7-(3-amino-1-pyrrolidinyl)-1-ethyl-6-fluoro-1,4-dihydro-4-oxo-1,8-naphthyridine-3-carboxylic acids having the general formula:

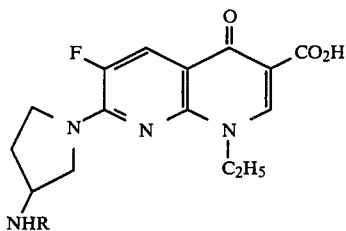

The compounds are disclosed to have antibacterial activity. The Journal of Medicinal Chemistry, 23, 1358 (1980) discloses certain substituted quinoline-3-carboxylic acids having the structural formula

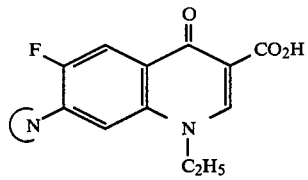

wherein 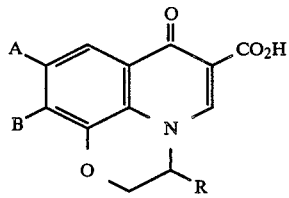 may be pyrrolidinyl. See also U.S. Pat. No. 4,146,719. The compounds are disclosed to have antibacterial activity.

European Patent Application No. 81 10 6747, Publication No. 047,005, published Mar. 10, 1982, discloses certain benzoxazine derivatives having the structural formula

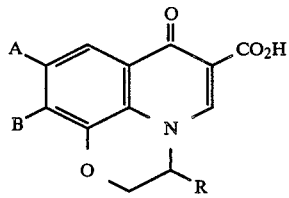

wherein A is halogen and B may be a cyclic amine substituent such as pyrrolidine, or piperidine.

Certain 7-heterocyclic substituted 1,8-naphthyridines are disclosed in Eur. J. Med. Chem. Chimica Therapeutica, 29, 27 (1977). U.S. Pat. Nos. 3,753,993 and 3,907,808 disclose certain 7-pyridylquinolines.

European patent publication no. 90 424 discloses 1-R-1,4-dihydro-4-oxo-6-fluoro-7-(Z=N)-quinolinecarboxylic acids and esters thereof where R is amino, lower alkylamino, 2-propenylamino or di-lower alkylamino and Z-N is preferably 1-piperazinyl or 4-lower alkyl-1-piperazinyl. The compounds are illustrated by the general formula

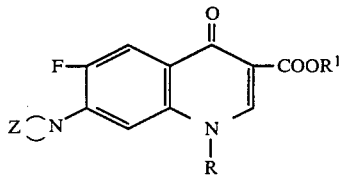

The references teach that these compounds possess antibacterial activity.

SUMMARY OF THE INVENTION

The invention in a first generic chemical compound aspect is a compound having the structural formula I

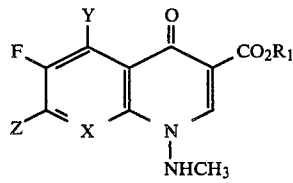

wherein
Z is

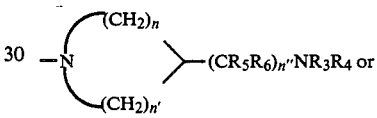

X is CH, CF or N; Y is hydrogen or amino;
n is 1, 2, 3, or 4;
n' is 1, 2, 3, or 4 wherein n+n' is a total of 2, 3, 4, or 5, and
n" is 0, 1, or 2; n''' is 0, 1, or 2;
n$^{iv}$ is 1, 2, or 3;
$R_1$ is hydrogen, alkyl having from one to six carbon atoms or a cation;
$R_3$ is hydrogen, alkyl having from one to four carbon atoms or cycloalkyl having three to six carbon atoms;
$R_4$ is hydrogen, alkyl from one to four carbon atoms, hydroxyalkyl having two to four carbon atoms, trifluoroethyl or $R_7CO$— wherein $R_7$ is alkyl having from one to four carbon atoms, or alkoxy having from one to four carbon atoms;
$R_5$ is hydrogen, or alkyl having from one to three carbon atoms;
$R_6$ is hydrogen or alkyl having from one to three carbon atoms, and the pharmaceutically acceptable acid addition or base salts thereof.

The preferred compounds of this invention are those wherein Z is

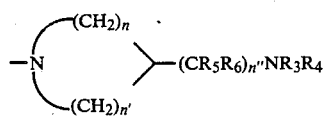

Also preferred compounds of this invention are those wherein Z is

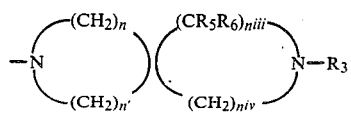

Other preferred compounds of this invention are those wherein Y is hydrogen. Other preferred compounds of this invention are those wherein X is CH or C—F.

Other preferred compounds of this invention are those wherein $R_1$ is hydrogen or a pharmaceutically acceptable base salt such as a metal or amine salt.

Other preferred compounds of this invention are those wherein n" is one, $R_3$ is hydrogen, methyl, ethyl, or n-propyl, and $R_4$, $R_5$, and $R_6$ are hydrogen.

The most preferred compounds are those wherein Y is hydrogen, X is CH or CF, Z is

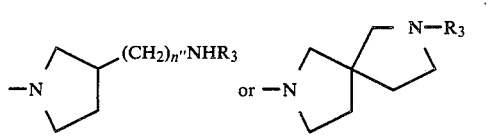

$R_1$ is hydrogen and $R_3$ is hydrogen, methyl, ethyl, 1- or 2-propyl, or a pharmaceutically acceptable acid addition or base salt thereof.

Particularly preferred species of the invention are the compounds having the names:

7-[3-[(ethylamino)methyl]-1-pyrrolidinyl]-6-fluoro-1-methylamino-1,4-dihydro-4-oxo-3-quinolinecarboxylic acid;

7-(3-amino-1-pyrrolidinyl)-6,8-difluoro-1,4-dihydro-1-methylamino-4-oxo-3-quinolinecarboxylic acid;

7-[3-[(ethylamino)methyl]-1-pyrrolidinyl]-6,8-di-fluoro-1,4-dihydro-1-methylamino-4-oxo-3-quinolinecarboxylic acid;

7-[3-(aminomethyl)-1-pyrrolidinyl]-6,8-difluoro-1,4-dihydro-1-methylamino-4-oxo-3-quinolinecarboxylic acid;

1,4-dihydro-6-fluoro-1-methylamino-7-(7-ethyl-2,7-diazaspiro[4.4]nonan-2-yl)-4-oxo-3-quinolinecarboxylic acid;

6,8-difluoro-1,4-dihydro-1-methylamino-7-(7-ethyl-2,7diazaspiro[4.4]nonan-2-yl)-4-oxo-3-quinolinecarboxylic acid;

1,4-dihydro-6-fluoro-1-methylamino-7-(7-methyl-2,7-diazaspiro[4.4]nonan-2-yl)-4-oxo-3-quinolinecarboxylic acid;

6,8-difluoro-1,4-dihydro-1-methylamino-7-(7-methyl-2,7-diazaspiro[4.4]nonan-2-yl)-4-oxo-3-quinolinecarboxylic acid;

1,4-dihydro-6-fluoro-1-methylamino-7-(2,7-diazaspiro[4.4]nonan-2-yl)-4-oxo-3-quinolinecarboxylic acid;

1,4-dihydro-6,8-difluoro-1-methylamino-7-(2,7-diazaspiro[4.4]nonan-2-yl)-4-oxo-3-quinolinecarboxylic acid;

7-(3-amino-1-pyrrolidinyl)-1,4-dihydro-6-fluoro-1-methylamino-4-oxo-3-quinolinecarboxylic acid;

1,4-dihydro-6-fluoro-1-methylamino-7-[3-[(methylamino)methyl]-1-pyrrolidinyl]-4-oxo-3-quinolinecarboxylic acid;

1,4-dihydro-6-fluoro-1-methylamino-7-[3-[(propylamino)methyl]-1-pyrrolidinyl]-4-oxo-3-quinolinecarboxylic acid;

1,4-dihydro-6,8-difluoro-1-methylamino-7-[3-[(propylamino)methyl]-1-pyrrolidinyl]-4-oxo-3-quinolinecarboxylic acid;

1,4-dihydro-6-fluoro-1-methylamino-7-[3-[(2-propylamino)methyl]-1-pyrrolidinyl]-4-oxo-3-quinolinecarboxylic acid;

1,4-dihydro-6,8-difluoro-1-methylamino-7-[3-[(2propylamino)methyl]-1-pyrrolidinyl]-4-oxo-3-quinolinecarboxylic acid;

7-[3-[(cyclopropylamino)methyl]-1-pyrrolidinyl]-1,4-dihydro-6-fluoro-1-methylamino-4-oxo-3-quinolinecarboxylic acid;

7-[3-[(cyclopropylamino)methyl]-1-pyrrolidinyl]-1,4-dihydro-6,8-difluoro-1-methylamino-4-oxo-3-quinolinecarboxylic acid;

1,4-dihydro-6-fluoro-1-methylamino-4-oxo-7-[3-[[(2,2,2-trifluoroethyl)amino]methyl]-1-pyrrolidinyl]-3-quinolinecarboxylic acid;

1,4-dihydro-6,8-difluoro-1-methylamino-4-oxo-7-[3[[(2,2,2-trifluoroethyl)amino]methyl]-1-pyrrolidinyl]-3-quinolinecarboxylic acid;

1,4-dihydro-6-fluoro-7-[3-[[(2-hydroxyethyl)amino]methyl]-1-pyrrolidinyl]-1-methylamino-4-oxo-3-quinolinecarboxylic acid;

1,4-dihydro-6,8-difluoro-7-[3-[[(2-hydroxyethyl)amino]methyl]-1-pyrrolidinyl]-1-methylamino-4-oxo-3-quinolinecarboxylic acid;

7-[3-(aminomethyl)-1-pyrrolidinyl]-1,4-dihydro-6-fluoro-1-methylamino-4-oxo-3-quinolinecarboxylic acid;

1,4-dihydro-6,8-difluoro-1-methylamino-7-[3-[(methylamino)methyl]-1-pyrrolidinyl]-4-oxo-3-quinolinecarboxylic acid, and the pharmaceutically acceptable acid addition or base salts thereof.

The following process for preparing compounds of the formula

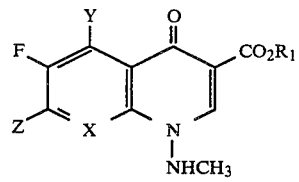

wherein $R_1$, X, Y, and Z are as defined for formula I which comprises reacting a compound having the following structural formula

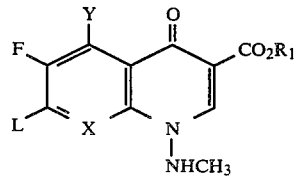

with an amine corresponding to the group Z wherein Z is the compound having the structural formula

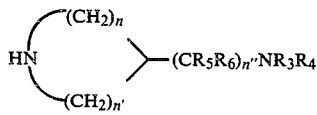

or

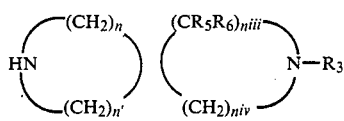 IIIa wherein all of the above terms are as defined in formulae I and L is a leaving group which is preferably fluorine or chlorine.

The invention also includes a pharmaceutical composition which comprises an antibacterially effective amount of a compound having structural formula I and the pharmaceutically acceptable salts thereof in combination with a pharmaceutically acceptable carrier. The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the invention having the structural formula I may be readily prepared by treating a corresponding compound having the structural formula II with the desired cyclic amine III or IIIa. For purposes of this reaction, the alkylamine substituent of Compound III or IIIa may, if desired, be protected by a group which renders it substantially inert to the reaction conditions. Thus, for example, protecting groups such as the following may be utilized:

carboxylic acyl groups such as formyl, acetyl, trifluoroacetyl;

alkoxycarbonyl groups such as ethoxycarbonyl, t-butoxycarbonyl, $\beta,\beta,\beta$-trichloroethoxycarbonyl, $\beta$-iodoethoxycarbonyl;

aryloxycarbonyl groups such as benzyloxycarbonyl, p-methoxybenzyloxycarbonyl, phenoxycarbonyl;

silyl groups such trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized.

The protecting group may be removed, after the reaction between Compound IV and Compound Va or Vb if desired, by procedures known to those skilled in the art. For example, the ethoxycarbonyl group may be removed by acid or base hydrolysis and the trityl group may be removed by hydrogenolysis.

The reaction between the compound of structural formula II and a suitably protected compound of formula III or IIIa may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of formula III or IIIa may be utilized as the acid acceptor.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group $R_4$ may be accomplished either before or after isolating the product, I. Alternatively, the protecting group $R_4$ need not be removed.

The starting compounds having structural formulae II are known in the art or, if new, may be prepared from known starting materials by standard procedures or by variations thereof. Thus the following compound is disclosed in the noted reference:

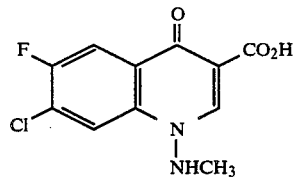

European Patent Publication 90 424A.

The 6,7,8-trifluoro-1,4-dihydro-1-methylamino-4-oxo-3-quinolinecarboxylic acid may also be prepared by a method described in European Patent Publication No. 90 424A. This compound may be converted to the corresponding 5-amino-6,7,8-trifluoro-1,4-dihydro-1-methylamino-4-oxo-3-quinolinecarboxylic acid by first nitrating the above compound with potassium nitrate and sulfuric acid then hydrogenating the nitro group catalytically with palladium on carbon according to known methods. An alternate method for preparing the above starting material is described in the Examples.

The compounds of the invention having structural formula III or IIIa are either known compounds or they may be prepared from known starting materials by standard procedures or by variations thereof. For example, 3-pyrrolidinemethanamines having the structural formula D

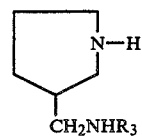

D may be readily prepared from the known starting material methyl 5-oxo-1-(phenylmethyl)-3-pyrrolidinecarboxylate, A, [J. Org. Chem., 26, 1519 (1961)] by the following reaction sequence.

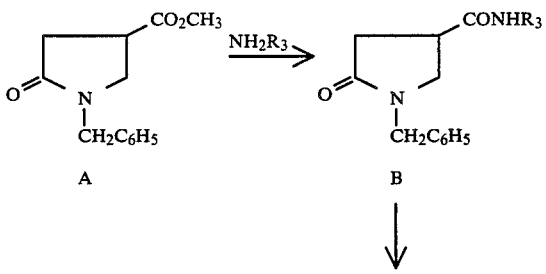

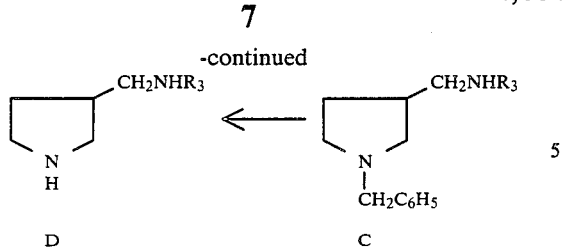

The compound wherein R₃ is hydrogen, namely 3-pyrrolidinemethanamine, has been reported in J. Org. Chem., 26, 4955 (1961).

Thus Compound A may be converted to the corresponding amide B by treatment with R₃NH₂; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when R₃=H in C, the primary amine function may be protected with a group R₄ as defined, hereinabove. For example, the primary amine function may be acylated with an acyl halide such as acetyl chloride by well known procedures. The primary amine function of C may also be converted to a carbamate ester such as the ethyl ester by treatment with ethyl chloroformate in the presence of a strong base such as 1,8-diazabicyclo[5.4.0]undec-7-ene in a convenient solvent such as methylene chloride. The benzyl group may next be removed, for example as described above for Compound C, thereby producing Compound D where R is —CO₂Et, which after conversion to a compound of the type Va or Vb may be reacted with a compound having the structural formula IV to thereby produce a corresponding compound having the structural formulae I. The —CO₂Et group may be removed by standard procedures.

Likewise spiroamino compounds represented by structural formula Vb may be readily prepared from the known starting material 3-ethoxycarbonyl-5-oxo-3-pyrrolidineacetic acid ethyl ester [J. Org. Chem., 46, 2757 (1981)] by the following reaction sequence.

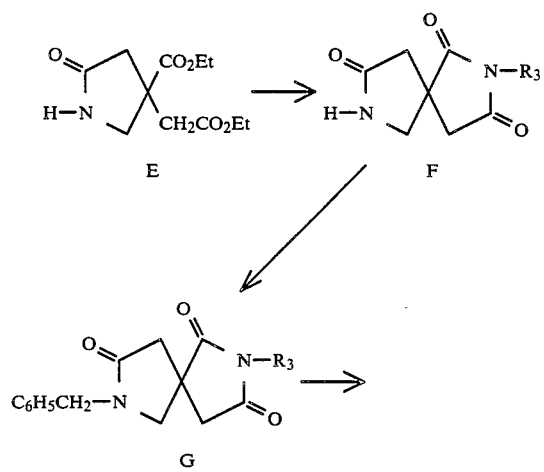

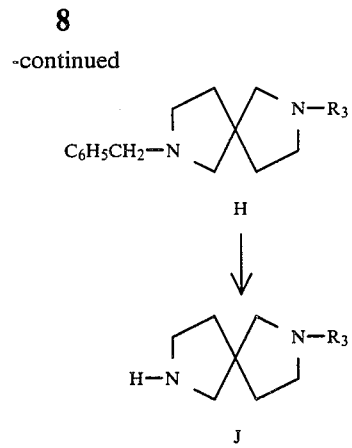

The compound 2,7-diazaspiro [4.4]nonane where R₃ is H is described in the above reference. Thus Compound E may be converted to the corresponding amide F by treatment with R₃NH₂, for example, methyl amine in water followed by benzylation which may be carried out with sodium hydride and benzyl chloride to give G. Reduction to the diamine H may be accomplished with lithium aluminum hydride. Subsequent debenzylation, for example, with hydrogen and 20% palladium on carbon catalyst produces the diamine J.

The compounds of the invention display antibacterial activity when tested by the microtitration dilution method as described in Heifetz, et al, Antimicr. Agents & Chemoth., 6, 124 (1974), which is incorporated herein by reference.

By use of the above referenced method, the followed minimum inhibitory concentration values (MICs in μg/ml) were obtained for representative compounds of the invention.

| | IN VITRO ANTIBACTERIAL ACTIVITY Minimal Inhibitory Concentration MIC (μg/ml) | | | |
|---|---|---|---|---|
| Organisms | Compound Ex. 1 | Compound Ex. 2 | Compound Ex. 3 | Compound Ex. 4 |
| Enterobacter cloacae MA 2646 | 6.3 | 0.8 | 0.2 | 1.6 |
| Escherichia coli Vogel | 12.5 | 0.2 | 0.2 | 1.6 |
| Klebsiella pneumoniae MGH-2 | 6.3 | 0.2 | 0.2 | 1.6 |
| Proteus rettgeri M 1771 | 25 | 0.4 | 1.6 | 1.6 |
| Pseudomonas aeruginosa UI-18 | 25 | 0.2 | 0.8 | 1.6 |
| Staphylococcus aureus H 228 | 12.5 | 3.1 | 0.4 | 1.6 |
| Staphylococcus aureus UC-76 | 0.2 | 0.4 | 0.2 | 0.2 |
| Streptococcus faecalis MGH-2 | 6.3 | 12.5 | 0.4 | 0.8 |
| Streptococcus pneumoniae SV-1 | 3.1 | 6.3 | 0.1 | 0.8 |
| Streptococcus pyogenes C-203 | 0.4 | 0.8 | 0.2 | 0.2 |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention. DBT-1 -17

The alkyl groups contemplated by the invention comprise both straight and branched carbon chains of from one to about three carbon atoms except when specifically stated to be greater than three carbon atoms. Representative of such groups are methyl, ethyl, propyl, isopropyl, and the like.

The cycloalkyl groups contemplated by the invention comprise those having three to six carbon atoms such as cyclopropyl, cyclobutyl, cyclopentyl, and cyclohexyl.

Certain compounds of the invention may exist in optically active forms. The pure D isomer, pure L isomer as well as mixtures thereof; including the racemic mixtures, are contemplated by the invention. Additional assymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantites of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the att. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

PREPARATION OF STARTING MATERIALS

EXAMPLE A

N-methyl-3-pyrrolidinemethanamine

N-methyl-5-oxo-1-(phenylmethyl)-3-pyrrolidinecarboxamide

A mixture of 100 g (0.43 mole) of methyl 5-oxo-1-(phenylmethyl)-3-pyrrolidinecarboxylate [J. Org. Chem., 26, 1519 (1961)], 500 ml methanol and 100 g (3.2 mole) of methylamine was heated at 100° C. in a pressure reactor for 16 hours. The reaction mixture was cooled and the ammonia and methanol were removed under reduced pressure. The residue was taken up in dichloromethane and washed with 3×100 ml 1N sodium hydroxide. The organic layer was dried over magnesium sulfate and the solvent removed at reduced pressure to give 88.3 g of N-methyl-5-oxo-1-(phenylmethyl)-3-pyrrolidinecarboxamide as a white solid, mp 82.5°–83.0° C.

This material was used in the next step.

N-methyl-1-(phenylmethyl)-3-pyrrolidinemethanamine

To a suspension of 37.40 g (1.00 mole) lithium aluminum hydride in 1000 ml tetrahydrofuran, was added a solution of 88.3 g (0.380 mole) of N-methyl-5-oxo-1-(phenylmethyl)-3-pyrrolidinecarboxamide in tetrafuran dropwise under nitrogen. The reaction was then refluxed overnight. The reaction flask was cooled in an ice bath and 37.4 ml of water, 37.4 ml of 15% sodium hydroxide and 112.2 ml of water were added. The precipitated solids were filtered and washed with hot ethanol. The combined filtrates were concentrated, then dissolved in dichloromethane, filtered, dried over magnesium sulfate, and the solvent evaporated under reduced pressure to give 68.68 g of N-methyl-1-(phenylmethyl)-3-pyrrolidinemethanamine as an oil. This material was used without further purification in the next step.

N-Methyl-3-pyrrolidinemethanamine

A mixture of 67.28 g (0.32 mole) of N-methyl-1-(phenylmethyl)-3-pyrrolidinemethanamine, 3 g of 20% palladium on carbon, and 600 ml of methanol was shaken in an atmosphere of hydrogen at about 50 psi and at room temperature for 18 hours. Another 3 g of 20% palladium on carbon was added and the hydrogenation continued for 6.5 hours. Another 3.0 g of 20% palladium on charcoal was added and the hydrogenation continued for another 4.5 hours. The catalyst was filtered and the filtrate evaporated under reduced pressure. The residue was distilled under vacuum (72°–76° C., 10.5 mm Hg) to give 8.32 g N-methyl-3-pyrrolidinemethanamine.

EXAMPLE B

N-Ethyl-3-pyrrolidinemethanamine

N-Ethyl-5-oxo-1-(phenylmethyl)-3-pyrrolidine-carboxamide

A mixture of 200 g (0.86 mole) of methyl 5-oxo-1-(phenylmethyl)-3-pyrrolidinecarboxylate [J. Org. Chem., 26, 1519 (1961)], 1000 ml methanol and 200 g (4.4 mole) of ethylamine was heated at 100° C. in a pressure reactor for 17.2 hours. The reaction mixture was cooled and the excess ethylamine and methanol were removed under reduced pressure. The residue was taken up in dichloromethane and washed with 3×150 ml 1N sodium hydroxide. The organic layer was dried over magnesium sulfate and the solvent removed at reduced pressure to give 104.6 g of N-ethyl-5-oxo-1-(phenylmethyl)-3-pyrrolidinecarboxamide as a white solid, mp 97°–99° C.

This material was used in the next step.

N-Ethyl-1-(phenylmethyl)-3-pyrrolidinemethanamine

To a suspension of 108.68 g (2.860 mole) lithium aluminum hydride in 800 ml tetrahydrofuran, was added a solution of 194.5 g (0.790 mole) of N-ethyl-5-oxo-1-(phenylmethyl)-3-pyrrolidinecarboxamide in 600 ml tetrahydrofuran dropwise under nitrogen. The reaction was then refluxed four hours. The reaction flask was cooled in an ice bath and 108 ml of water, 108 ml of 15% sodium hydroxide, and 324 ml of water were added. The precipitated solids were filtered and washed with hot ethanol. The combined filtrates were concentrated, then dissolved in dichloromethane, filtered, dried over magnesium sulfate, and the solvent evaporated under reduced pressure to give 151.9 g of N-ethyl-1-(phenylmethyl)-3-pyrrolidinemethanamine as an oil.

This material was used without further purification in the next step.

N-Ethyl-3-pyrrolidinemethanamine

A mixture of 151.65 g (0.695 mole) of N-ethyl-1-(phenylmethyl)-3-pyrrolidinemethanamine, 5 g of 20% palladium on carbon, and 1100 ml of ethanol was shaken in an atmosphere of hydrogen at about 50 psi and at room temperature for 21.6 hours. Another 5 g of 20% palladium on carbon was added and the hydrogenation continued for 24 hours. The catalyst was filtered and the filtrate evaporated under reduced pressure. The residue was distilled under vacuum (88°–91° C., 11.5 mm Hg) to give 66.0 g N-ethyl-3-pyrrolidinemethanamine.

EXAMPLE C

N-(2,2,2-Trifluoroethyl)-3-pyrrolidinemethanamine

5-Oxo-1-(phenylmethyl)-N-(2,2,2-trifluoroethyl)-3-pyrrolidinecarboxamide

A mixture of 21.9 g (0.100 mole) 5-oxo-1-(phenylmethyl)-3-pyrrodlidinecarboxylic acid in 150 ml tetrahydrofuran, was cooled to 0° C. in an ice bath under nitrogen and 24.32 g (0.150 mole) carbonyl diimidazole was added. The reaction was stirred at 0° C. for 30 minutes, then at room temperature for 30 minutes. A solution of 13.55 g (0.100 mole) of 2,2,2-triflouroethylamine hydrochloride, 15.22 g (0.100 mole) 1,8-diazabicyclo[5.4.0]undec-7-ene and 100 ml tetrahydrofuran was added. The reaction was stirred at room temperature overnight. The solvent was removed at reduced pressure. The residue was taken up in dichloromethane and washed 3×150 ml saturated sodium bicarbonate. The organic layer was dried over magnesium sulfate and the solvent removed under reduced pressure. The product was purified by column chromatography on silica with ethyl acetate to give 8.50 g of 5-oxo-1-(phenylmethyl)-N-(2,2,2-trifluoroethyl)-3-pyrrolidinecarboxamide, mp 110°–112° C.

This material was used in the next step.

1-(Phenylmethyl)-N-(2,2,2-trifluoroethyl)-3-pyrrolidinemethanamine

A mixture of 8.50 g (28.3 mole) of 5-oxo-1-(phenylmethyl)-N-(2,2,2-trifluoroethyl)-3pyrrolidinecarboxamide in 100 ml tetrahydrofuran was added dropwise to 3.22 g (84.9 mmole) of lithium aluminum hydride in 50 ml tetrahydrofuran. The reaction was refluxed two hours, then stirred at room temperature overnight. The reaction was cooled in an ice bath and 3.2 ml of water, 3.2 ml of 15% sodium hydroxide, and 9.6 ml of water were added. The precipitated salts were filtered and washed with hot ethanol. The combined filtrates were concentrated under reduced pressure. The residue was taken up in dichloromethane, filtered, and dried over magnesium sulfate. The solvent was removed at reduced pressure to give 7.15 g of 1-(phenylmethyl)-N-(2,2,2-trifluoroethyl)-3-pyrrolidinemethanamine.

This material was used without further purification in the next step.

N-(2,2,2-trifluoroethyl)-3-pyrrolidinemethanamine

A mixture of 7.15 g (26.3 mmole) 1-(phenylmethyl)-N-(2,2,2-trifluoroethyl)-3-pyrrolidinemethanamine 100 ml of methanol and 0.7 g of 20% palladium on carbon was shaken in an atmosphere of hydrogen at about 50 psi and at room temperature for 24 hours. The catalyst was filtered and the filtrate evaporated under reduced pressure. The residue was distilled under vacuum (63°–65° C., 2.8 mm Hg) to give 2.55 g of N-(2,2,2-trifluoroethyl)-3-pyrrolidinemethanamine.

EXAMPLE D

N-Propyl-3-pyrrolidinemethanamine

5-Oxo-1-(phenylmethyl)-N-propyl-3-pyrrolidinecarboxamide

To a solution of 10.96 g (50 mmole) of 5-oxo-1-(phenylmethyl)-3-pyrrolidinecarboxylic acid in 150 ml of acetonitrile was added 9.73 g (60 mmole) of carbonyldiimidazole. The reaction was heated to 60° C. for one hour, cooled to room temperature and treated with 4.13 g (70 mmole) of n-propylamine. After stirring for two hours, the solvent was removed in vacuo and the residue partitioned between ether and water. The organic layer was washed with water, 1N hydrochloric acid, dried over magnesium sulfate, filtered, and evaporated invacuo to give 12.0 g of 5-oxo-1-(phenylmethyl)-N-propyl-3-pyrrolidinecarboxamide, mp 86°–87° C.

1-(Phenylmethyl)-N-propyl-3-pyrrolidinemethanamine

To a suspension of 8.2 g (0.2 mole) of lithium aluminum hydride in 150 ml of dry tetrahydrofuran was added portionwise, 12.0 g (45.6 mmole) of solid 5-oxo-1-(phenylmethyl)-N-propyl-3-pyrrolidinecarboxamide. When the addition was complete, the reaction mixture was stirred at room temperature for 18 hours and then at reflux for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 9.6 g of 1-(phenylmethyl)-N-propyl-3-pyrrolidine methanamine, as a heavy syrup.

This material was used for the next step without further purification.

N-Propyl-3-pyrrolidinemethanamine

A mixture of 14.0 g (60.0 mmole) of 1-(phenylmethyl)-N-propyl-3-pyrrolidinemethanamine, 1.0 g of 20% palladium on carbon and 140 ml of methanol was shaken in an atmosphere of hydrogen at about 50 psi and room temperature for 24 hours. The catalyst was removed by filtering through Celite, the filtrate concentrated and distilled in vacuo to give 7.1 g of N-propyl-3-pyrrolidinemethanamine, bp 49°–50° C./0.25 mm.

EXAMPLE E

N-Cyclopropyl-3-pyrrolidinemethanamine

5-Oxo-1-(phenylmethyl)-N-cyclopropyl-3-pyrrolidinecarboxamide

To a solution of 16.4 g (75 mmole) of 5-oxo-1-(phenylmethyl)-3-pyrrolidinecarboxylic acid in 150 ml of acetonitrile was added 13.8 g (85 mmole) of carbonyldiimidazole. The reaction was heated to 60° C. for one hour, cooled to room temperature and treated with 4.85 g (85 mmole) of cyclopropylamine. The reaction was stirred at room temperature for 18 hours, the solvent removed in vacuo and the residue partitioned between chloroform and water. The organic layer was washed with water, 1N hydrochloric acid, dried over magnesium sulfate, filtered, and evaporated in vacuo to give 18.3 g of 5-oxo-1-(phenylmethyl)-N-cyclopropyl-3-pyrrolidinecarboxamide, mp 94°–96° C. 1-(Phenylmethyl)-N-cyclopropyl-3-pyrrolidine-methanamine To a suspension of 8.2 g (0.20 mole) of lithium aluminum hydride in 150 ml of dry tetrahydrofuran was added portionwise 18.0 g (70.0 mmole) of solid 5-oxo-1-(phenylmethyl)-N-cyclopropyl-3-pyrrolidinecarboxamide. When the addition was complete, the reaction mixture was stirred at room temperature for 18 hours and then at reflux for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 16.0 g of 1-(phenylmethyl)-N-cyclopropyl-3-pyrrolidinemethanamine as a heavy oil. This was used for the next step without further purification.

N-Cyclopropyl-3-pyrrolidinemethanamine

A mixture of 13.6 g (59.0 mmol) of 1-(phenylmethyl)-N-cyclopropyl-3-pyrrolidinemethanamine, 0.5 g of 20% palladium on carbon and 140 ml of methanol was shaken in an atmosphere of hydrogen at about 50 psi and room temperature for 24 hours. The catalyst was removed by filtering through Celite, the filtrate concentrated and distilled in vacuo to give 6.3 g of N-cyclopropyl-3-pyrrolidinemethanamine, bp 88°–90° /13 mm.

EXAMPLE F

N-(2-Propyl)-3-pyrrolidinemethanamine

5-Oxo-1-(phenylmethyl)-N-(2-propyl)-3-pyrrolidinecarboxamide

To a solution of 16.4 g (75.0 mmole) of 5-oxo-1-(phenylmethyl)-3-pyrrolidinecarboxylic acid in 150 ml of acetonitrile was added 13.8 g (85.0 mmole) of 1,1'-carbonyldiimidazole. The reaction was heated to 60° C. for one hour, cooled to room temperature and treated with 5.0 g (85 mmole) of isopropylamine. The reaction was stirred at room temperature for 18 hours, the solvent removed in vacuo and the residue partitioned between chloroform and water. The organic layer was washed with water, 1N hydrochloric acid, dried over magnesium sulfate and evaporated in vacuo to give 18.6 g of 5-oxo-1-(phenylmethyl)-N-(2-propyl)3-pyrrolidinecarboxamide, mp 122°–124° C.

1-(Phenylmethyl)-N-(2-propyl)-3-pyrrolidinemethanamine

To a suspension of 8.2 g (0.2 mole) of lithium aluminum hydride in 150 ml of dry tetrahydrofuran was added portionwise, 18.3 g (70.0 mmole) of solid 5-oxo-1-(phenylmethyl)-N-(2-propyl)-3-pyrrolidinecarboxamide. When the addition was complete, the reaction mixture was stirred at room temperature for 18 hours and then refluxed for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 15.6 g of 1-(phenyl-methyl)-N-(2-propyl)-3-pyrrolidinemethanamine as a heavy syrup.

This material was used for the next step without further purification.

N-(2-Propyl)-3-pyrrolidinemethanamine

A mixture of 13.4 g (58.0 mmol) of 1-phenylmethyl-N-(2-propyl)-3-pyrrolidinemethanamine, 1.0 g of 20% palladium on carbon and 130 ml of methanol was shaken in an atmosphere of hydrogen at about 50 psi and room temperature for 24 hours. The catalyst was removed by filtration through Celite; the filtrate concentrated and distilled in vacuo to give 6.3 g of N-(2-propyl)-3-pyrrolidinemethanamine, bp 58°–60° C./3.5 mm.

EXAMPLE G 2-[(3-pyrrolidinylmethyl)amino]ethanol

N-(2-hydroxyethyl)-5-oxo-1-(phenylmethyl)-3-pyrrolidinecarboxamide

A mixture of 46.7 g (1200 mole) of methyl 5-oxo-1-(phenylmethyl)-3-pyrrolidinecarboxylate (J. Org. Chem., 26, 1519 (1961)], 36.7 g (1600 mole) 2-aminoethanol and 500 ml methanol were refluxed overnight. The reaction was cooled to room temperature and the solvent removed at reduced pressure. The residue was taken up in dichloromethane and extracted 3×100 1N sodium hydroxide. The aqueous layer was taken to pH 5, extracted with 3×150 ml dichloromethane, then taken to pH 8 and again extracted with 3×150 ml dichloromethane. The aqueous layer was concentrated at reduced pressure and the resulting slurry stirred in dichloromethane. The salts were filtered off. The combined organic layers were dried over magnesium sulfate, the solvent removed at reduced pressure to yield 47.9 g of N-(2-hydroxyethyl)-5-oxo-1-(phenylmethyl)-3-pyrrolidinecarboxamide as an oil. This was used in the next step without further purification.

2-[[[1-(phenylmethyl)-3-pyrrolidinyl]methyl]amino] ethanol.

A mixture of 46.66 g (0.178 mole) of N-(2-hydroxyethyl)-5-oxo-1-(phenylmethyl)-3-pyrrolidinecarboxamide in 200 ml of tetrahydrofuran was added dropwise to a slurry of 20.25 g (0.534 mole) of lithium aluminum hydride in 150 ml tetrahydrofuran. The reaction was refluxed three hours, then cooled in an ice bath. The work up consisted of sequential addition of 20 ml water, 20 ml 15% sodium hydroxide then 60 ml water. The reaction was filtered and the precipitate washed with ethanol. The filtrate was concentrated at reduced pressure, the residue taken up in dichloromethane, dried over magnesium sulfate, and the solvent removed at reduced pressure to give 32.31 g of 2-[[[1-(phenylmethyl)-3-pyrrolidinyl]methyl]amino]ethanol as an oil. This material was used in the next step without further purification.

2-[(3-pyrrolidinylmethyl)amino]ethanol

A mixture of 32.32 g of 2-[[[1-(phenylmethyl)3-pyrrolidinyl]methyl]amino]ethanol, 330 ml of methanol and 3 g of 20% palladium on charcoal was shaken in an atmosphere of hydrogen at about 50 psi and at room temperature for 18 hours. The solvents were then removed at reduced pressure. The residue was distilled under vacuum (bp 129°–131° C. 1.5 mm Hg) to give 11.43 g of 2-[(3-pyrrolidinyl methyl)amino] ethanol.

EXAMPLE H

2-Methyl-2,7-diazaspiro[4.4]nonane Dihydrochloride

2-Methyl-2,7-diazaspiro[4.4]nonane-1,3,8-trione

A solution of 20.3 g (0.084 mole) 3-ethoxycarbonyl-5-oxo-3-pyrrolidineacetic acid, ethyl ester [J. Org. Chem. 46, 2757 (1981)]in 40 ml of 40% aqueous methylamine was stirred at room temperature overnight, then placed in an oil bath and gradually heated to 220° C. over 30 minutes allowing volatiles to distill from the open flask. The crude product was crystallized from ethanol to afford 12.56 g of 2-methyl-2,7-diazaspiro[4.4]nonane-1,3,8-trione, mp 201°–204° C.

2-Methyl-7-(phenylmethyl)-2,7-diazaspiro[4.4]-nonane-1,3,8-trione

A solution of 1.82 g (10 mmol) 2-methyl-2,7diazaspiro[4.4]nonane-1,3,8-trione in 20 ml N,N-dimethylformamide was added gradually under a nitrogen atmosphere to 0.050 g (10.4 mmol) of 50% oil suspension of sodium hydride which had been previously washed twice with toluene and covered with 10 ml N,N-dimethylformamide. After stirring one hour there was added 1.40 g (11 mmol) of benzyl chloride and stirring was continued overnight at room temperature. After concentrating to a small volume in vacuo, the residue was diluted with 40 ml water and extracted twice with dichloromethane. The combined organic phase was washed with water, dried over magnesium sulfate, and evaporated to give a solid. Crystallization from toluene-hexane afforded 1.74 g of 2-methyl-7-(phenylmethyl)-2,7-diazaspiro[4.4]nonane-1,3,8-trione, mp 157°–158° C.

2-Methyl-7-(phenylmethyl)-2,7-diazaspiro[4.4]nonane Dihydrochloride

A solution of 1.36 g (5.0 mmol) 2-methyl-7-(phenylmethy)-2,7-diazaspiro[4.4]nonane-1,3,8-trione in 50 ml tetrahydrofuran was added dropwise to a suspension of 0.95 g (25 mmol) lithium aluminum hydride in 30 ml tetrahydrofuran. Ihe mixture was stirred overnight at room temperature, refluxed one hour, cooled, and treated dropwise with 0.95 ml water, 0.95 ml 15% sodium hydroxide solution and 2.8 ml water. After removal of the inorganic solids by filtration, the filtrate was concentrated in vacuo to give a syrup which was dissolved in isopropanol and treated with excess 6N hydrogen chloride in isopropanol. Crystallization afforded 0.97 g of 2-methyl-7-(phenylmethyl)-2,7-diazaspiro[4.4]nonane dihydrochloride, mp 233-234° C.

2-Methyl-2,7-diazaspiro[4.4]nonane Dihydrochloride

A solution of 2-methyl-7-(phenylmethyl)-2,7-diazaspiro-[4.4]nonane dihydrochloride in 150 ml of methanol with 1.0 g 20% palladium on carbon catalyst was hydrogenated at 50 psi for two days. After filtration, the filtrate was concentrated to a thick syrup which crystallized on addition of acetonitrile to give 11.50 g of 2-Methyl-2,7diazaspiro[4.4]nonane dihydrochloride, softened at 164° C. and melted at 168°–170° C. EXAMPLE I 2-Ethyl-2,7-diazaspiro[4.4]nonane Dihydrochloride
2-Ethyl-2,7-diazaspiro[4.4]nonane-1,3,8-trione A suspension of 24.33 g (0.100 mmole) 3-ethoxycarbonyl-5-oxo-3-pyrrolidineacetic acid, ethyl ester in an excess of 2N sodium hydroxide, was stirred three hours at room temperature, acidified with dilute hydrochloric acid, and evaporated to dryness in vacuo. The product, 3-carboxy-5-oxo-3-pyrrolidineacetic acid, was taken up in isopropyl alcohol, separated from insoluble sodium chloride by filtration, concentrated to a syrup and dissolved in 100 ml 70% ethylamine. The solution was gradually heated in an oil bath up to 230° C. allowing volates to distill and then maintained at 230°–240° C. for ten minutes. After cooling, the product was crystallized from isopropyl alcohol to afford 10.12 g of 2-ethyl2,7-diazaspiro[4.4]nonane-1,3,8-trione, mp 168°–169° C.

2-Ethyl-7-(phenylmethyl)-2-7-diazaspiro-[4.4]-nonane-1,3,8-trione

A suspension of sodium hydride (2.20 g of 60% oil suspension (0.055 mole) washed with toluene) in 50 ml N,N-dimethylformamide was treated gradually with a solution of 10.0 g (0.051 mole) 2-ethyl-2,7diazaspiro[4.4-]nonane-1,3,8-trione in 100 ml N,N-dimethylformamide. After stirring 15 minutes, there was added dropwise 6.4 ml (0.055 mole) benzyl chloride and the mixture was stirred overnight, concentrated in vacuo and shaken with water-methylene chloride. The organic layer was dried, evaporated, and the product crystallized from toluene-hexane to afford 11.11 g of 2-ethyl-7-(phenylmethyl)-2-7-diazaspiro[4.4]nonane-1,3,8-trione, mp 125°–126.5° C.

2-Ethyl-7-(phenylmethyl)-2,7-diazaspiro[4.4]nonane Dihydrochloride

A solution of 11.00 g (0.0385 mole) 2-ethyl-7-(phenylmethyl)-2,7-diazaspiro[4.4]nonane-1,3,8-trione in 100 ml tetrahydrofuran was added dropwise to a suspension of 6.00 g (0.158 mole) lithium aluminium hydride in 250 ml tetrahydrofuran. After stirring overnight, the mixture was refluxed one hour, cooled, and treated dropwise with 6 ml water, 6 ml 15% sodium hydroxide, and 18 ml water. Inorganic solids were separated by filtration and the filtrate was concentrated, taken up in ether, dried with magnesium sulfate, and reevaporated. The resulting syrup was dissolved in isopropyl alcohol and treated with excess hydrogen chloride in isopropyl alcohol to afford 9.63 g of 2-ethyl-7-(phenylmethyl)-2,7-diazaspiro[4.4]nonane dihydrochloride, mp 196°–198° C. (dec).

2-Ethyl-2,7-diazaspiro[4.4]nonane Dihydrochloride A solution of 9.50 g (0.030 mole)
2-ethyl-7-(phenylmethyl)-2,7-diazaspiro[4.4]nonane dihydrochloride in 100 ml methanol was hydrogenated with 1.0 g 20% palladium on carbon catalyst at 50 psi for 22 hours. After filtration, the solution was concentrated to a syrup and crystallized from acetonitrile to afford 6.66 g of 2-ethyl-2,7-diazaspiro[4.4]nonane dihydrochloride, mp 168°–172° C.

EXAMPLE J 1,1-Dimethylethyl (3-Pyrrolidinyl)carbamate
1,1-Dimethylethyl
[1-(Phenylmethyl)-3-pyrrolidinyl]carbamate A solution of 77.0 g (0.44 mole) of 3-amino-1-(phenylmethyl)pyrrolidine [J. Med. Chem., 24, 1229 (1981)], 440 ml (0.44 mole) 1.0N sodium hydroxide and 600 ml of tertiary butyl alcohol was treated dropwise with 98.2 g (0.45 mole) of di-tertiarybutyl dicarbomate. The reaction was stirred at room temperature for 18 hours and the solvent removed in vacuo. The residue was partitioned between ether and water. The aqueous layer was reextracted with ether, the combined ether layers were washed with water, dried (MgSO$_4$), filtered and evaporated on a steam bath replacing the ether with petroleum ether. The crystals which formed were removed by filtration, washed with ether/petroleum ether (1:1), and dried in vacuo to give 84.8 g of 1,1-dimethylethyl [1-(phenylmethyl)-3-pyrrolidinyl]carbamate, mp 114°–115°. A second crop (16.7 g) was obtained by concentrating the filtrate.

1,1-Dimethylethyl (3-Pyrrolidinyl)carbamate

A mixture of 101.5 g (0.37 mole) of 1,1-dimethylethyl[1-(phenylmethyl)-3-pyrrolidinyl]carbamate, 5.0 g of 20% Palladium on carbon and 1 liter of tetrahydrofuran was shaken in an atmosphere of hydrogen at about 50 psi and room temperature for 24 hours. The catalyst was removed by filtering through Celite, and the filtrate was concentrated in vacuo to give 6.8 g of 1,1-dimethylethyl (3-pyrrolidinyl)carbamate which solidified upon standing and was of sufficient purity to be used as is for the ensuing steps.

EXAMPLE K

Preparation of
1-Methylamino-6,7,8-trifluoro-1,4-dihydro-4-oxo-3-quinolinecarboxylic Acid
2,3,4,5-Tetrafluorobenzoylacetic acid, Ethyl Ester To 25.2 g (0.117 mol) of sodium 2,3,4,5-tetrafluorobenzoate, prepared as a dry powder from 2,3,4,5tetrafluorobenzoic acid [J. Org. Chem. 29, 2381 (1961)] and aqueous sodium hydroxide with concentration to dryness, was added 400 ml of dry ether and the suspension was cooled to 0° C. Slowly 25 ml (~2.5 equivalents) of oxalyl chloride in 50 ml of ether was added and the mixture brought to room temperature where it was maintained for 2.0 hours. It was filtered and concentrated to remove low boiling impurities. The residue was dissolved in 100 ml of ether and placed in an addition funnel.

Meanwhile, 2.9 g (0.119 mol) of magnesium turnings were treated with 100 ml of absolute ethanol and 0.3 ml of carbon tetrachloride. To this mixture was added 18.6 ml (0.12 mol) of diethyl malonate in 75 ml of ether at a rate to keep the temperature just below reflux. When addition was complete, the reaction was refluxed for two hours. At −20° C., the ethereal acid chloride was slowly added. When addition was complete, the reaction was brought to 0° C. over 18 hours. The mixture was poured into dilute hydrochloric acid and was extracted into dichloromethane which was dried over magnesium sulfate and concentrated. The residue was then treated with 340 mg of p-toluenesulfonic acid in 600 ml of water at 100° C. for two hours with rapid stirring. The oil was extracted into dichloromethane, dried over magnesium sulfate and concentrated. The residue was purified by column chromatography (Silica gel, using toluene:hexane:ether, 4:5:1), to give 18.5 g of a reddish oil. This material was triturated with pentane to give 10.2 g of 2,3,4,5-tetrafluorobenzoylacetic acid, ethyl ester, mp 49°–51° C.

2-[2-(Ethoxycarbonyl)-3-oxo-3-(1,2,3,4-tetrafluorophenyl)-1-propenyl]-1-methylhydrazinecarboxylate, 1,1-Dimethyl Ester To 3.0 g (11.33 mmol) of 2,3,4,5-tetrafluorobenzoylacetic acid, ethyl ester was added 2.49 g of triethylorthoformate and 2.76 g of acetic anhydride. The mixture was heated to 150° C. for 2.5 hours and was then cooled to 80° C. The volitile materials were removed at 0.4 mm Hg for one hour. The residue was then cooled to 45° C. and diluted with 25 ml of isopropyl alcohol. To this solution was added 1.65 g of 1-methylhydrazinecarboxylate, 1,1-dimethylethyl ester (Acta Chemica Scandinavica 22, 1, 1968) in 25 ml of isopropyl alcohol. The mixture was stirred overnight, diluted with 30 ml of pentane and filtered to give 3.09 g of 2-[2-(ethoxycarbonyl)-3-oxo-3-(1,2,3,4-tetrafluorophenyl)-1-propenyl]-1-methylhydrazinecarboxylate, 1,1-dimethylethyl ester as a white solid, mp 130°–131° C.

1-[[(1,1-Dimethylethoxy)carbonyl]methylamino]-6,7,8-trifluoro-1,4-dihydro-4-oxo-3-quinolinecarboxylic acid, Ethyl Ester To 3.09 g (7.35 mmol) of 2-[2-(ethoxycarbonyl)-3-oxo-3-(1,2,3,4-tetrafluorophenyl)-1-propenyl-1-methylhydrazinecarboxylate, 1,1-dimethyethyl ester in 100 ml of dry dioxane was added 0.36 g (1.02 equivalent) of sodium hydride (50% dispersion) which was pentane washed prior to addition. The mixture was then refluxed overnight and was left standing at room temperature for 24 hours. The mixture was concentrated to a thick oil, taken up in dichloromethane, filtered and extracted with water twice. The dichloromethane was dried (MgSO4) and concentrated to a viscous oil which crystallized upon addition of pentane to give 2.39 g of 1-[[(1,1-dimethylethoxy)-carbonyl]methylamino]-6,7,8-trifluoro-1,4-dihydro-4-oxo-3-quinolinecarboxylic acid, ethyl ester, mp 99.5°–102° C.

6,7,8-Trifluoro-1,4-dihydro-1-methylamino-4-oxo-3quinolinecarboxylic acid

To 2.00 g (5.0 mmol) of 1-[[(1,1-dimethylethoxy)carbonyl]methylamino]-6,7,8-trifluoro-1,4-dihydro-4-oxo-3-quinolinecarboxylic acid, ethyl ester was added 35 ml of acetic acid and 15 ml of 2N hydrochloric acid. The mixture was placed on a steam bath for 2.5 hours, was diluted with 15 ml of water, and was cooled. The solids were filtered to give 1.09 g of 6,7,8-trifluoro-1,4-dihydro-1-methylamino-4-oxo-3quinolinecarboxylic acid, mp 237°–238° C.

EXAMPLE 1

7-[3-[(Ethylamino)methyl]-1-pyrrolidinyl]-6-fluoro-1-methylamino-1,4-dihydro-4-oxo-3-quinolinecarboxylic Acid A mixture of 0.81 g (3 mmol) 7-chloro-6-fluoro-1-methylamino-1,4-dihydro-4-oxo-3-quinolinecarboxylic acid (European Patent No. 0,090,424) and 1.54 g (12 mmol) -[(ethylamino)methyl]-pyrrolidine in 5 ml pyridine was refluxed 19 hours, concentrated to a syrup in vacuo, and diluted with ether to afford a yellow solid. The crude product was dissolved in water, titrated to pH 1.5 with dilute hydrochloric acid, and crystallized from methanol to afford 0.64 g 7-[3-[(ethylamino)methyl]pyrrolidine]-6-fluoro-1-methylamino-1,4-dihydro-4-oxo-3-quinolinecarboxylic acid, mp 280° C. with decomposition.

EXAMPLE 2

7-(3-Amino-1-pyrrolidinyl)-6,8-difluoro-1,4-dihydro-1-methylamino-4-oxo-3-quinolinecarboxylic Acid To 1.00 g (3.68 mmol) of 6,7,8-trifluoro-1,4-dihydro-1-methylamino-4-oxo-3-quinolinecarboxylic acid in 10 ml of acetonitrile was added 0.56 g (1.0 equivalent) of 1,8-diazobicyclo-[5,4,0]undec-7-ene and 0.68 g of 1,1-dimethylethyl 3-pyrrolidinylcarbamate. The mixture was refluxed for one hour and stirred at room temperature overnight. The solids were filtered and washed with ether to give 0.92 g of 7-[3-[[(1,1dimethylethoxy)-carbonyl]amino]-1-pyrro-lidinyl]-6,8-difluoro-1,4-dihydro-1-(methylamino)-4-oxo-3quinolinecarboxylic acid. A portion of this material (0.38 g) was treated with 10 ml of trifluoroacetic acid for 2 hours and was concentrated. The residue was taken up in aqueous sodium hydroxide to pH 12.5 and then treated with hydrochloric acid to pH 7.0. The solids were filtered to give 0.24 g of 7-(3-amino-1-pyrrolidinyl)-6,8-difluoro-1,4-dihydro-1-methylamino-4-oxo-3-quinolinecarboxylic acid, mp 210°–211° C.

EXAMPLE 3

7-[3-[(Ethylamino)methyl]-1-pyrrolidinyl]-6,8-difluoro-1,4-dihydro-1-methylamino-4-oxo-3-quinolinecarboxylic acid To 0.75 g (2.75 mmol) of the 6,7,8-trifluoro-1,4-dihydro-1-methylamino-4-oxo-3-quinolinecarboxylic acid in 15 ml of acetonitrile was added 0.44 g (1.05 equivalent) of 1,8-diazobicyclo[5.4.0]undec-7-ene, and 0.352 g (1.0 equivalent) of N-ethyl-3-pyrrolidinemethanamine. The mixture was refluxed for one hour and then stirred at room temperature overnight. The solids were filtered to give 0.68 g of 7-[3-[(ethylamino)methyl]-1-pyrrolidinyl]-6,8-difluoro-1,4-dihydro-1-methylamino-4-oxo-3-quinolinecarboxylic acid, mp 222°–224° C.

EXAMPLE 4

7-[3-(Aminomethyl)-1-pyrrolidinyl]-6,8-difluoro-1,4-dihydro-1-methylamino-4-oxo-3-quinolinecarboxylic acid To 0.75 g (2.75 mmol) of the 6,7,8-trifluoro-1,4-dihydro-1-methylamino-4-oxo-3-quinolinecarboxylic acid in 15 ml of acetonitrile was added 0.44 g (1.05 equivalents) of 1,8-diazobicyclo[5.4.0]undec-7-ene and 0.275 g (1.0 equivalents) of 3-pyrrolidinemethanamine [J. Org. Chem., 26, 4955 (1961)]. The mixture was refluxed for one hour and stirred at room temperature overnight. The solids were filtered to give 0.72 g of 7-[3-(aminomethyl)-1-pyrrolidinyl[-6,8-difluoro-1,4-dihydro-1-methylamino-4-oxo-3-quinolinecarboxylic acid, mp 150°–180° C. slow dec.

EXAMPLE 5

1,4-Dihydro-6-fluoro-1-methylamino-7-(7-ethyl-2,7-diazaspiro[4.4]nonan-2-yl)-4-oxo-3-quinolinecarboxylic acid may be prepared by the method in Example 1 by using 2-ethyl-2,7-diazaspiro[4.4]nonane as the reacting amine.

EXAMPLE 6

6,8-Difluoro-1,4-dihydro-1-methylamino-7-(7-ethyl-2,7-diazasprio[4.4]nonan-2-yl)-4-oxo-3-quinolinecarboxylic acid may be prepared by the method in Example 3 by using 2-ethyl-2,7-diazaspiro[4.4]nonane as the reacting amine.

EXAMPLE 7

1,4-Dihydro-6-fluoro-1-methylamino-7-(7-methyl-2,7diazaspiro[4.4]nonan-2-yl)-4-oxo-3-quinolinecarboxylic acid may be prepared by the method in Example 1 by using 2-methyl-2,7-diazaspiro[4.4]nonane as the reacting amine.

EXAMPLE 8

6,8-Difluoro-1,4-dihydro-1-methylamino-7-(7 ethyl-2,7-diazaspiro[4.4]nonan-2-yl)-4-oxo-3-quinolinecarboxylic acid may be prepared by the method in Example 3 by using 2-ethyl-2,7-diazaspiro[4.4]nonane as the reacting amine.

EXAMPLE 9

1,4-Dihydro-6-fluoro-1-methylamino-7-(2,7-diazaspiro[4.4]nonan-2-yl)-4-oxo-3-quinolinecarboxylic acid may be prepared by the method in Example 1 by using 2,7 diazaspiro[4.4]nonane [J. Org. Chem. 46, 2757 (1981)] as the reacting amine.

EXAMPLE 10

1,4-Dihydro-6,8-difluoro-1-methylamino-7-(2,7-diazaspiro[4.4]nonan-2-yl)-4-oxo-3-quinolinecarboxylic acid may be prepared by the method in Example 3 by using 2,7-diazaspiro[4.4]nonan [J. Org. Chem. 46, 2757 (1981)]as the reacting amine.

EXAMPLE 11

7-(3-Amino-1-pyrrolidinyl)-1,4-dihydro-6-fluoro-1-methylamino-4-oxo-3-quinolinecarboxylic acid may be prepared by the method in Example 2 by using 1,1-dimethylethyl 3-pyrrolidinylcarbamate as the reacting amine.

EXAMPLE 12

1,4-Diydro-6-fluoro-1-methylamino-7-[3-[(methylamino)methyl]-1-pyrrolidinyl]-4-oxo-3-quinolinecarboxylic acid may be prepared by the method in Example 3 by using N-methyl-3-pyrrolidinemethanamine as the reacting amine.

EXAMPLE 13

1,4-Dihydro-6,8-difluoro-1-methylamino-7-[3-[(methylamino)methyl]-1-pyrrolidinyl]-4-oxo-3-quinolinecarboxylic acid may be prepared by the method in Example 3 by using N-methyl-3-pyrrolidinemethanamine as the reacting amine.

EXAMPLE 14

1,4-Dihydro-6-fluoro-1-methylamino-7-[3-[(propylamino)methyl]-1-pyrrolidinyl]-4-oxo-3-quinolinecarboxylic acid may be prepared by the method in Example 1 by using N-propyl-3-pyrrolidinemethanamine as the reacting amine.

EXAMPLE 15

1,4-Dihydro-6,8-difluoro-1-methylamino-7-[3-[(propylamino)methyl]-1-pyrrolidinyl]-4-oxo-3-quinolinecarboxylic acid may be prepared by the method in Example 3 by using N-propyl-3-pyrrolidinemethanamine as the reacting amine.

EXAMPLE 16

1,4-Dihydro-6-fluoro-1-methylamino-7-[3-[(2-propylamino)methyl]-1-pyrrolidinyl]-4-oxo-3quinolinecarboxylic acid may be prepared by the method in Example 1 by using N-(2-propyl)-3pyrrolidinemethanamine as the reacting amine.

EXAMPLE 17

1,4-Dihydro-6,8-difluoro-1-methylamino-7-[3-[(2propylamino)methyl]-1-pyrrolidinyl]-4-oxo-3quinolinecarboxylic acid may be prepared by the method in Example 3 by using N-(2-propyl)-3-pyrrolidinemethanamine as the reacting amine.

EXAMPLE 18

7-[3-[(Cyclopropylamino)methyl]-1-pyrrolidinyl]-1,4-dihydro-6-fluoro-1-methylamino-4-oxo-3-quinolinecarboxylic acid may be prepared by the method in Example 1 by using N-cyclopropyl-3pyrrolidinemethanamine as the reacting amine.

EXAMPLE 19

7-[3-[(Cyclopropylamino)methyl]-1-pyrrolidinyl]-1,4-dihydro-6,8-difluoro-1-methylamino-4-oxo-3quinolinecarboxylic acid may be prepared by the method in Example 3 by using N-cyclopropyl-3pyrrolidinemethanamine as the reacting amine.

EXAMPLE 20

1,4-Dihydro-6-fluoro-1-methylamino-4-oxo-7-[3-[[(2,2,2-trifluoroethyl)amino]methyl]-1-pyrrolidinyl]-3-quinolinecarboxylic acid may be prepared by the method in Example 1 by using N-(2,2,2-trifluoroethyl)-3-pyrrolidinemethanamine as the reacting amine.

p EXAMPLE 21

1,4-Dihydro-6,8-difluoro-1-methylamino-4-oxo-7-[3-[[(2,2,2-trifluoroethyl)amino]methyl]-1pyrrolidinyl]-3-quinolinecarboxylic acid may be prepared by the method in Example 3 by using N-(2,2,2-trifluoroethyl)-3-pyrrolidinemethanamine as the reacting amine.

EXAMPLE 22

1,4-Dihydro-6-fluoro-7-[3-[[(2-hydroxyethyl)amino]methyl]-1-pyrrolidinyl]-1-methylamino-4-oxo-3-quinolinecarboxylic acid may be prepared by the method in Example 1 by using 2-[(3-pyrrolidinylmethyl)amino]ethanol as the reacting amine.

EXAMPLE 23

1,4-Dihydro-6,8-difluoro-7-[3-[[(2-hydroxyethyl)amino]methyl]-1-pyrrolidinyl]-1-methylamino-4-oxo-3-quinolinecarboxylic acid can by prepared by the method in Example 3 by using 2-[(3-pyrrolidinylmethyl)amino]ethanol as the reacting amine.

EXAMPLE 24

7-[3-(Aminomethyl)-1-pyrrolidinyl]-1,4-dihydro-6-fluoro-1-methylamino-4-oxo-3-quinolinecarboxylic acid may be prepared by the method in Example 1 by using 3-pyrrolidinemethanamine as the reacting amine.

We claim:
1. A compound of the formula

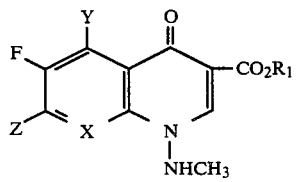

wherein Z is

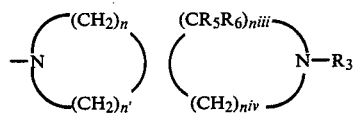

wherein R₁ is hydrogen or an alkyl having from one to six carbon atoms or a cation; X is CF or CH, Y is hydrogen or amino; R₃ is hydrogen, alkyl having from one to four carbon atoms or cycloalkyl having three to six carbon atoms; R₅ is hydrogen or alkyl having from one to three carbon atoms; R₆ is hydrogen or an alkyl having from one to three carbon atoms; n is one, two, three, or four, n' is one, two, three, or four wherein n+n' is a total of two, three, four, or five, n''' is zero, one or two, n^{iv} is one, two, or three and the pharmaceutically accpetable acid addition or base salts thereof.

2. A compound of the formula

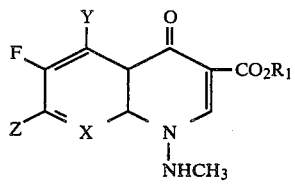

wherein
Y is hydrogen:
Z is

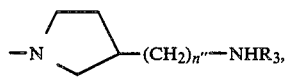

in which n'' is one and R₃ is hydrogen, methyl, ethyl, 1- or 2-propyl; X is C—F and R₁ is hydrogen or a pharmaceutically acceptable base salt thereof.

3. A compound of the formula

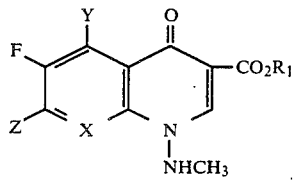

wherein Z is

X is C—F or CH; R₃ is hydrogen, methyl, or ethyl; R₁ is hydrogen, alkyl having from one to six carbon atoms or a cation, and the pharmaceutically acceptable acid addition or base salts thereof.

4. The compound 7-[3-[(ethylamino)methyl]-1-pyrrolidinyl]-6,8-difluoro-1,4-dihydro-1-methylamino-4-oxo-3-quinolinecarboxylic acid.

5. The compound 7-[3-(aminomethyl)-1-pyrrolidinyl]-6,8-difluoro-1,4-dihydro-1-methylamino-4-oxo-3-quinolinecarboxylic acid.

6. A pharmaceutical composition comprising an antibacterially effective amount of a compound as claimed in claim 1 or 2 together with a pharmaceutically acceptable carrier.

7. The method of treating bacterial infections in mammals which comprises administering to said mammal a pharmaceutical composition as claimed in claim 6.

* * * * *

UNITED STATES PATENT AND TRADEMARK OFFICE
CERTIFICATE OF CORRECTION

PATENT NO. : 4,604,401
DATED : Aug. 5, 1986
INVENTOR(S) : Thomas F. Mich, Townley P. Culbertson, John M. Domagala It is certified that error appears in the above—identified patent and that said Letters Patent is hereby corrected as shown below:

Column 22, line 63-67: Structure should be closer together.

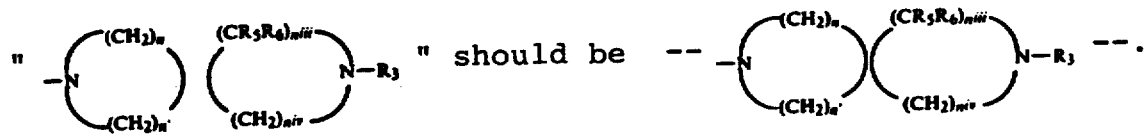

Column 24, line 2: $\overset{Y}{|}$ should be deleted.

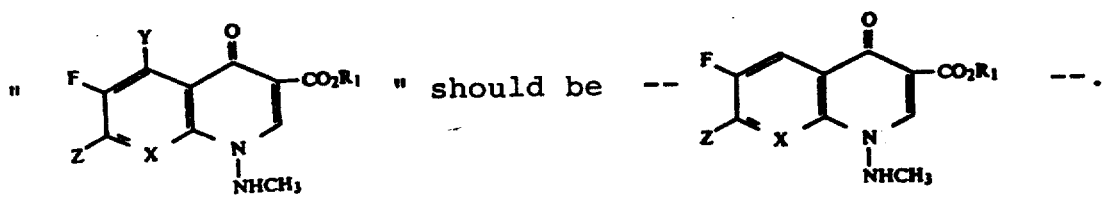

Signed and Sealed this

Fourteenth Day of October, 1986

[SEAL]

Attest:

DONALD J. QUIGG

Attesting Officer

Commissioner of Patents and Trademarks